US00PP23954P2

(12) United States Plant Patent
Kordes

(10) Patent No.: US PP23,954 P2
(45) Date of Patent: Oct. 8, 2013

(54) MINATURE ROSE PLANT NAMED 'KORPOT001'

(50) Latin Name: *Rosa hybrida*
Varietal Denomination: KORpot001

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 89 days.

(21) Appl. No.: 13/385,489

(22) Filed: Feb. 21, 2012

(51) Int. Cl.
*A01H 5/00* (2006.01)

(52) U.S. Cl.
USPC ..... Plt./120

(58) Field of Classification Search
USPC ..... Plt./120
See application file for complete search history.

(56) References Cited

PUBLICATIONS

Pluto UPOV PBR QZ citation for 'KORpot001' Feb. 22, 2011.*

* cited by examiner

*Primary Examiner* — Wendy C Haas

(57) ABSTRACT

A new and distinct variety of rose with long lasting, novel cream apricot flowers, and attractive foliage with good disease resistance. It exhibits above average vigor with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot001'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2006. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot001'.

SUMMARY OF THE INVENTION

The new rose plant may be distinguished from its seed parent, an 'un-named seedling', by the following combination of characteristics:

1. 'KORpot001' has cream apricot cup shaped flowers, whereas the 'un-named seedling' has cream white flowers with high centered buds.
2. 'KORpot001' has a moderately compact growth habit, whereas the 'un-named seedling' has an upright habit.

The new rose plant may be distinguished from its pollen parent, an 'un-named seedling', by the following combination of characteristics:

1. 'KORpot001' has cream apricot flowers, whereas the 'un-named seedling' has copper yellow flowers.
2. 'KORpot001' has large flowers, whereas the 'un-named seedling' has medium sized flowers.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot001' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot001' was selected in May, 2007 from the seedling beds to be asexually propagated for further evaluation. The first asexual propagation of 'KORpot001' was done by rooting cuttings in June, 2007 at the inventor's nursery in Offenseth-Sparrieshoop, Germany.

This initial and other subsequent propagations conducted in controlled environments demonstrate that 'KORpot001' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpot001'.

DETAILED BOTANICAL DESCRIPTION

The following is a description of 'KORpot001', as observed growing in October, 2011 in a nursery in Jackson County, Oreg. on plants 6 months of age. Color references are made using The Royal Horticultural Society (London, England) Colour Chart, 2001 except where common terms of color are used.

For a comparison, several physical characteristics of the rose variety 'KORpedia', a rose variety from the same inventor described and illustrated in U.S. Plant Pat. No. 19,638 and issued on Jan. 20, 2009 are compared to 'KORpot001' in Chart 1.

CHART 1

| Characteristic | 'KORpot001' | 'KORpedia' |
|---|---|---|
| General tonality | Yellow-Orange Group 20C | Yellow Group 2D |
| Pistil count | 25-30 | Approximately 90 |
| Petal count | 70-85 | 30-35 |

Parents: Seed Parent: 'Un-named seedling'. Pollen Parent: 'Un-named seedling'.

Classification:

*Botanical classification.*—*Rosa hybrida* 'KORpot001'.

*Commercial classification.*—Miniature rose.

FLOWER AND FLOWER BUD

Blooming habit: Recurrent.

Flower bud:

*Size.*—Upon opening, 20 mm in length from base of receptacle to distal end of bud and 14 mm diameter at its widest point.

*Bud form.*—Short. Pointed ovoid.

*Bud color.*—As sepals first unfold, bud color is Yellow-Green Group 149D. When ¼ open, the upper surface of petals is Yellow-White Group 158D with a basal zone of Yellow Group 9C, and the lower surface is Yellow-Orange Group 18D. Guard petals have intonations of Yellow-Green Group 145C.

*Sepals.*—Color: Upper surface: Yellow-Green Group 144A. Lower surface: Yellow-Green Group 144A. Size: Average 15-35 mm (l)×7-9 mm (w). Shape: Strong foliaceous appendages on three of the five sepals. Apex: Three sepals are cirrose and two are apiculate. Base: Flat at union with receptacle. Quantity: Five. Surface texture: Upper side: Heavily pubescent. Lower surface: Light pubescence with stipitate glands. Margins: With stipitate glands.

Receptacle:

*Surface.*—Smooth.

*Color.*—Yellow-Green Group 144B.

*Shape.*—Funnel.

*Size.*—8 mm (h)×7 mm (w).

Peduncle:

*Surface.*—With fine hairs and stipitate glands.

*Length.*—60 to 80 mm average length.

*Diameter.*—2 to 3 mm average diameter.

*Color.*—Yellow-Green Group 144B.

*Strength.*—Strong.

*Borne.*—Singularly.

Flower bloom:

*Fragrance.*—Very light fruit and citrus scent.

*Duration.*—On the plant 12 to 14 days. Long lasting. As a cut flower, 6 to 7 days. Senesced petals drop away cleanly.

*Size.*—Large for a miniature rose. When open, the average flower diameter is 80 mm and the average flower height is 35 mm.

*Form.*—Shape of flower when viewed from the side: Upon opening, upper part: Flattened convex. Upon opening, lower part: Flattened convex. Open flower, upper part: Flat. Open flower, lower part: Concave.

Color:

*Upon opening, petals.*—Outermost petals: Outer Side: Yellow-White Group 158D. Inner Side: Yellow-White Group 158D with a basal zone of Yellow Group 10B. Innermost petals: Outer Side: Yellow-Orange Group 23D. Inner Side: Yellow-Orange Group 22D.

*Upon opening, basal petal spots.*—Basal petal spot, outermost petals: Outer Side: None observed. Inner Side: No distinct basal spot. Basal zone is Yellow Group 12A. Basal petal spot, innermost petals: Outer Side: Yellow Group 12C. Inner Side: Yellow Group 12B.

*After opening, petals.*—Outermost petals: Outer Side: White Group 155B. Inner Side: Yellow-White Group 158C with basal zone of Yellow Group 8A. Innermost petals: Outer Side: Yellow-Orange Group 20C. Inner Side: Yellow-Orange Group 20C with intonations of Yellow Group 9B in the basal zone.

*After opening, basal petal spots.*—Basal petal spot, outermost petals: Outer Side: Yellow Group 3D. Inner Side: Yellow Group 3D. Basal petal spot, innermost petals: Outer Side: Yellow Group 9C. Inner Side: Yellow Group 9C.

General tonality: On open flower Yellow-Orange Group 20C. No change in the general tonality at the end of the fourth day. Afterwards, general tonality is Yellow-Orange Group 18C.

Petals:

*Petal count.*—Very double.

*Average range.*—Approximately 70 to 85 petals under normal conditions.

*Petal reflex.*—Petals reflex somewhat.

*Petal edge.*—Entire.

*Petal shape.*—Obovate. Apex shape is round. Shape of base is cuneate.

*Petal size.*—30-40 mm (l)×30 mm (w).

*Thickness.*—Thick.

*Petal arrangement.*—Not Formal.

Petaloids:

*Petaloid count.*—Average of 2-5 per flower.

*Petaloid size.*—Petaloids are 10-15 mm (l)×3-4 mm (w).

*Petaloid color.*—Color of inner side is Yellow-Orange Group 18D. Color of outer side is Yellow-Orange Group 16D.

*Petaloid texture.*—Thick.

*Margins.*—Reflexed and ruffled.

*Petaloid shape.*—Most commonly oblanceolate, with some petaloids highly irregular. Apex: Obtuse. Base: Pointed.

Reproductive organs:

*Pistils.*—Approximately 25-30 present. Stigmas: Location: Slightly superior in position to anthers. Color:

Yellow Group 4C. Styles: Length: About 8 mm long. Color: Green-Yellow Group 1D with intonations of Red Group 46C.

*Stamens*.—Approximately 20 on average and regularly arranged. Anthers: Size: Average 0.5 mm long. Pollen: Generally present. Color: Greyed-Orange Group 163A. Filaments: Color: Green-Yellow Group 1C. Length: 4 mm.

THE PLANT

Growth: Above average vigor.

Plant habit: Compact upright habit. When grown as a 13 cm pot plant, the average plant height is 25 cm and the average plant width is 20 cm.

Blooming: Floriferous.

Stems:

*Stem color*.—Young wood: Yellow-Green Group 144A. Older wood: Yellow-Green Group 144A.

*Stem surface*.—Young wood: Smooth. Older wood: Smooth.

Prickles: Present.

*Incidence*.—Average of 3 per each 10 cm of stem.

*Size*.—Average length: 6 mm.

*Color*.—Immature prickles: Green-Yellow Group 161. Prickles not observed on mature wood.

*Shape*.—Linear.

*Anthocyanin*.—On young prickles, Greyed-Red Group 182C.

Leaves and leaflets: Normally 5 leaflets on normal leaves in middle of the stem.

*Venation pattern*.—Pyramidal net pattern.

*Leaf size*.—110 mm (l)×80 mm (w).

*Abundance*.—Average.

*Texture*.—Thin. Upper side of leaflet: Semi-glossy. Under side of leaflet: Matte.

*Color, mature foliage*.—Upper Leaf Surface: Green Group 137A. Lower Leaf Surface: Green Group 138B.

*Color, juvenile foliage*.—Upper Leaf Surface: Yellow-Green Group 144B. Lower Leaf Surface: Yellow-Green Group 144B.

*Anthocyanin intonation*.—Present. Intonations of Greyed-Purple Group 183B present on leaflet margins and upper leaf surface.

Stipules:

*Size*.—8 mm long, 3 mm from distal tip to distal tip.

*Stipule color*.—Yellow-Green Group 144A.

*Margins*.—With stipitate glands.

*Shape*.—Apex: Apiculate. Base: Winged.

Petiole:

*Length*.—Average 12 mm.

*Diameter*.—Average 1 mm.

*Petiole color*.—Yellow-Green Group 144A.

*Underneath*.—With small, fine prickles and stipitate glands.

*Margins*.—With stipitate glands.

Petiole rachis:

*Length*.—Average 18-20 mm.

*Diameter*.—Average 1 mm.

*Color*.—Yellow-Green Group 144A.

*Margins*.—With stipitate glands.

*Underneath*.—With stipitate glands and a few small prickles.

Leaflets:

*Size*.—Average size of the terminal leaflet is 50 mm (l)×30 mm (w).

*Shape*.—Ovate. Base: Obtuse. Apex: Acute.

*Margins*.—Serrated.

*Surface*.—Upper surface: Moderately glossy. Lower surface: Matte.

*Texture*.—Thin.

*Arrangement*.—Odd pinnate.

*Venation*.—Reticulate.

Hips/seed formation: Not observed.

Winter hardiness: Unknown.

Disease resistance: Good resistance to powdery mildew (*Sphaerotheca pannosa*) and Botrytis (*Botrytis cinerea*) diseases under normal growing conditions.

I claim:

1. A new and distinct variety of rose plant, as described and illustrated herein.

* * * * *

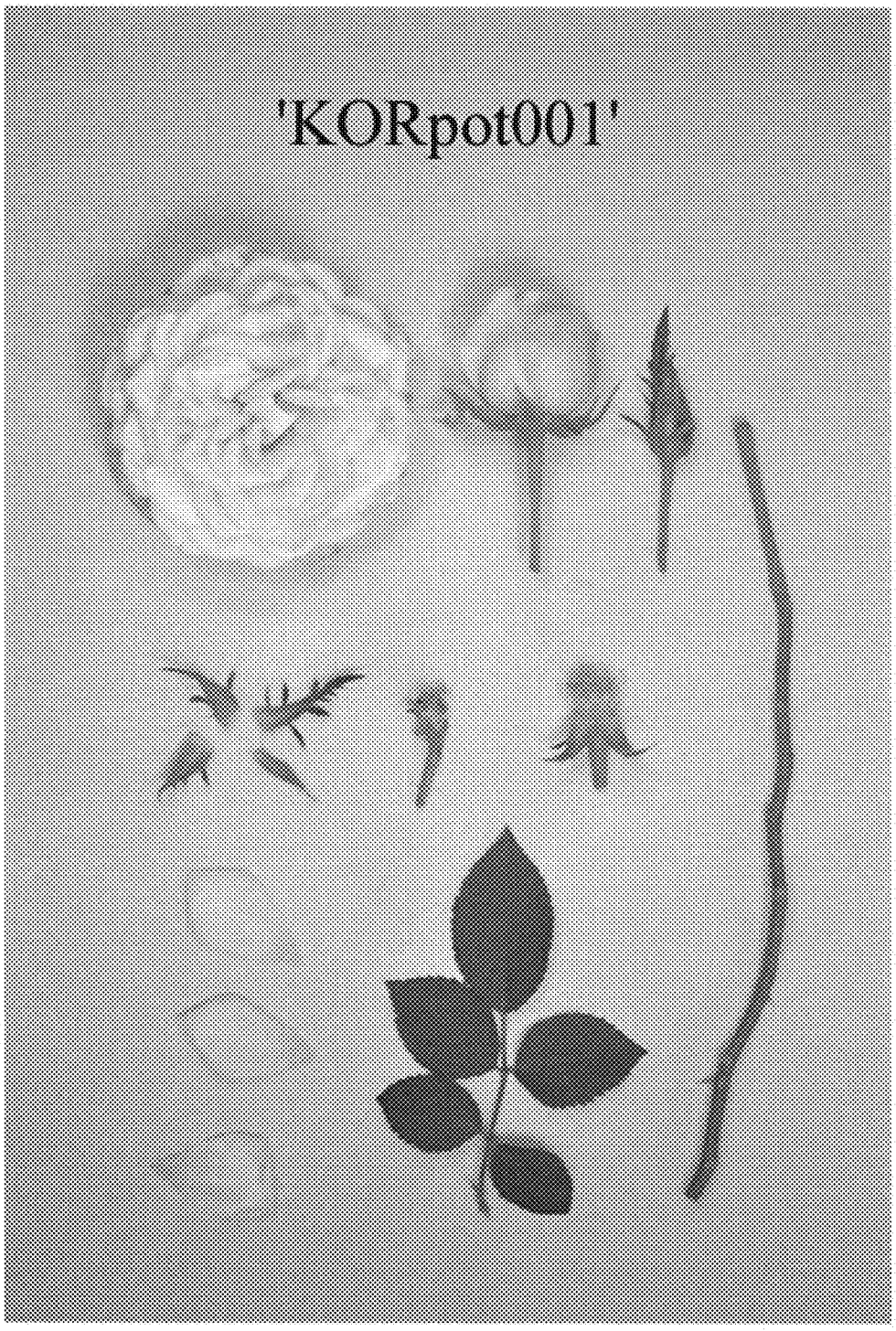
'KORpot001'